US00PP21248P2

(12) United States Plant Patent
Slaughter et al.

(10) Patent No.: US PP21,248 P2
(45) Date of Patent: Aug. 31, 2010

(54) ***PRUNUS* ROOTSTOCK, 'CORNERSTONE'**

(50) Latin Name: ***P. dulcis*×*P. persica***
Varietal Denomination: Cornerstone

(75) Inventors: John K. Slaughter, Fresno, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 12/386,894

(22) Filed: Apr. 24, 2009

(51) Int. Cl.
*A01H 5/00* (2006.01)

(52) U.S. Cl. ..... Plt./180
(58) Field of Classification Search ..... Plt./180
See application file for complete search history.

(56) References Cited

U.S. PATENT DOCUMENTS

PP5,173 P 1/1984 Hansen ..... Plt./30

*Primary Examiner*—Annette H Para
(74) *Attorney, Agent, or Firm*—Wells St. John P.S.

(57) ABSTRACT

A new and distinct variety of rootstock is described and which is characterized as to novelty by its lower incidence and expression of crown gall (*agrobacterium tuberfaciens*).

1 Drawing Sheet

BACKGROUND OF THE NEW VARIETY

The present invention relates to a new, novel and distinct variety of *Prunus* rootstock, (*P. dulcis*×*P. persica*), and which has been denominated varietally as 'Cornerstone'.

The present variety of rootstock resulted from an on-going program of fruit and nut tree breeding. The purpose of this program is to improve the commercial quality of available deciduous fruit and nut varieties, and rootstocks, by creating and releasing promising selections of *prunus, malus* and *regia* species. To this end we make both controlled and hybrid cross pollinations each year in order to produce seedling populations from which improved progenies are evaluated and selected.

The seedling 'Cornerstone' was originated by us from a population of seedlings grown in our experimental orchards located near Fowler, Calif. The seedlings, grown on their own roots, were the result of a controlled cross made in 1987, of the unpatented almond tree 'Titan', which was used as the seed parent; and an unpatented peach tree 'Nemared' which was used as the pollen parent. The seedlings resulting from the cross were then planted into an experimental site known to contain high populations of nematodes which are a major pest problem for commercial plantings of *prunus* plant material. One seedling, which is the present variety, exhibited especially desirable characteristics, and was marked, '677RS' for subsequent observation. After the 1984 growing season, the new, present variety, was selected for advanced evaluation and repropagation.

The new seedlings (approximately 50) resulting from the aforementioned cross were then later planted into an experimental site known to contain high populations of root knot nematodes (*Meloidogyne javanica* and *Meloidogyne incognita*) species, and grown for one year. These two nematodes can be a major pest effecting commercial rootstocks and are commonly found in the sandy soils of the Northern, Central and Southern San Joaquin valleys of the California interior. These seedlings were planted in December of 1988 and removed in January of 1989.

Of the approximately 50 seedlings that were subjected to the root knot nematode planting, 3 seedlings were later identified as having no root galling from the root knot nematodes, and further had an absence of galls from *agrobacterium tuberfaciens*. These same promising seedlings exhibited well advanced root development and an adequate tree vigor. Further re-propagations and evaluations showed that the seedlings exhibited a significantly low incidence of crown gall. Moreover, one of these three seedlings exhibited a purple-green leafed character (commonly referred to as red leaf), and as such was selected for further repropagation, testing and evaluation to determine if this rootstock might impart these same characteristics to scion varieties when compared to the rather common 'Nemaguard', 'Nemared' and Titan (all unpatented) or 'Hansen' 536 (U.S. Plant Pat. No. 5,173) commercial rootstocks. Subsequent evaluations have confirmed that these same subsequent characteristics have been passed on to subsequent re-propagations of trees.

ASEXUAL REPRODUCTION

Asexual reproduction of the new and distinct variety of rootstock was accomplished by us by taking cuttings from the original selection and planting the same in our experimental orchard which is located near Fowler, Calif. in 1987. Subsequent evaluations have shown those asexual reproductions run true to the original tree. All characteristics of the original tree were established, and appear to be transmitted through succeeding asexual propagations.

SUMMARY OF THE VARIETY

'Cornerstone' is a new and distinct variety of rootstock which appears to be quite useful for almond, peach, nectarine, plum and some apricot varieties. The present variety appears novel in view of its considered resistance to infection by *m. incognita* and *m. jovinica,* both of which are common root knot nematodes which reside in the sandy soils of many valley locations throughout California. The present new rootstock variety transplants easily and displays medium chilling requirements of approximately 650 to 700 hours. Additionally, the new rootstock 'Cornerstone' has a generally more compact growth habit when compared to the almond, and peach hybrid rootstock tree 'Hansen 536' (U.S. Plant Pat. No. 5,173), and which shows a lower incidence of mortality due to phytophora. In relative comparison to the 'Titan' almond tree (unpatented), which is the seed parent of same, the variety 'Cornerstone' exhibits red leaves whereas the variety 'Titan' exhibits green leaves. Additionally, the present variety does not exhibit the degree of sensitivity to crown gall (*agrobacterium tumafaciens*) that the trees as described in U.S. Plant Pat. No. 5,173 does. Further, the inventors have discovered that when peach and nectarine varieties are grafted onto the 'Cornerstone' rootstock, the fruit produced generally exhibits larger fruit size than when either variety is grafted onto more conventional and unpatented rootstock such as 'Nemaguard' or Nemared' (both unpatented).

BRIEF DESCRIPTION OF THE DRAWINGS

The accompanying drawing, which is provided, is a color photograph of the new variety of rootstock tree. The photograph depicts four typical leaves, two of which show the dorsal coloration thereof, and two of which show the ventral coloration. The photograph also displays a sample vegetative shoot bearing typical leaves. Also the photographs depicts two typical scions with buds, showing its variable coloration. The photograph also depicts two complete pits with the flesh removed, a typical pit which has been split substantially along the longitudinal plane with the seed left in one of the halves; and two mature seeds. The colors in the photograph are as nearly true as is reasonably possible in a color representation of this type. Due to chemical development, processing, and printing, the leaves and fruit depicted in these photographs may or may not be accurate when compared to the actual specimen. For this reason, future color references should be made to the color plates (Royal Horticultural Society) and descriptions provided.

NOT A COMMERCIAL WARRANTY

The following detailed description has been prepared to solely comply with the provisions of 35 U.S.C. § 112, and does not constitute a commercial warranty, (either expressed or implied), that the present variety will in the future display the botanical or other varietal characteristics as set forth, hereinafter. Therefore, this disclosure may not be relied upon to support any future legal claims including, but not limited to, beach of warranty of merchantability, fitness for any particular purpose or infringement which is directed, in whole, or in part, to the present variety.

DETAILED DESCRIPTION

Referring more specifically to the botanical details of this new and distinct variety of rootstock, the following has been observed during the ninth season under the ecological conditions prevailing at orchards located near the town of Fowler, county of Fresno, state of Calif. All major color code designations are by reference to the RHS Colour Chart (Fourth Edition) provided by The Royal Horticultural Society of Great Britain. Common color names are also occasionally used.

Tree:

*Size.*—Generally—Considered medium-large as compared to other common commercial rootstock cultivars. The tree of the present variety, which was 9 years old, was pruned to a height of approximately 430 cm. to about 450 cm. at maturity. This characteristic can vary based upon specific growing conditions, pruning, pest control, nutritional and other cultural practices. Therefore, this aspect of the tree cannot, alone distinguish the tree from other cultivars.

*Vigor.*—Considered vigorous. The present variety grew from about 150 cm. to 170 cm. in height during the first growing season. The new rootstock variety was pruned to a height of approximately 140 cm. during the first dormant season, and primary scaffolds were then selected for the desired tree structure.

*Productivity.*—Self-fruitful although seed production is not considered an economic aspect or claim of the current variety and is therefore not distinctive of this new variety.

*Bearer.*—Regular, as observed during the past 12 years.

*Form.*—Spreading and somewhat basitonic in shape.

*Density.*—Considered moderately dense. However, this characteristic is highly dependant upon cultural practices.

*Hardiness.*—The present tree was grown and evaluated in USDA Hardiness Zone 9. Winter chilling requirements of the new and novel tree are approximately 650 hours below 7.0 degrees C. The new variety appears to be hardy under typical central San Joaquin Valley climatic conditions.

Trunk:

*Diameter.*—Approximately 25 cm. in diameter when measured at a distance of approximately 10 cm above the soil level, at the end of the ninth growing season. This characteristic can vary depending upon specific growing conditions, and other cultural practices and is therefore not distinctive of the present variety.

*Bark texture.*—Considered moderately smooth.

*Lenticels.*—Numerous flat, oval lenticels are present. The lenticels range in size from approximately 4.0 mm. to about 6.0 mm. in width; and from about 1 mm. to about 2.5 mm. in height.

*Lenticel color.*—Considered a greyish brown, (RHS Grey-Brown Group N 199A).

*Bark coloration.*—Variable, but it is generally considered to be a medium brown, (RHS Greyed-Orange Group 175A).

Branches:

*Size.*—Considered moderately large for rootstock.

*Diameter.*—Average as compared to other rootstock varieties. The branches have a diameter of about 15 centimeters when measured during the $9^{th}$ year after grafting.

*Surface texture.*—Moderately smooth, and appearing furrowed with some scarf skin appearing on wood which is several years old.

*Crotch angle.*—Primary branches are considered variable between about 42 degrees to about 50 degrees from the horizontal axis. This particular characteristic is not considered distinctive of the variety, however.

*Current season shoots.*—Surface texture—Substantially glabrous.

*Internode length.*—Approximately 2.7 cm. to about 3.1 cm. This tree characteristic is highly dependent upon plant nutrition, soil quality, pruning and tree care, and therefore is not distinctive of the variety.

*Color of mature branches.*—Dull brown, (RHS Grey-Brown Group N199C).

*Current seasons shoots.*—Color—Drab green, (RHS Yellow-Green 152 A). The color of new shoot tips is considered a brownish red (RHS Greyed-Red Group 178 A).

Leaves:

*Size.*—Considered medium large for the species. Leaf measurements have been taken from vigorous, upright, current-season growth, at approximately mid-shoot.

*Leaf length.*—Approximately 165 mm. to about 190 mm.

*Leaf width.*—Approximately 30 mm. to about 47 mm.

*Leaf base shape.*—Slightly oblique relative to the leaf longitudinal axis.

*Leaf form.*—Lanceloeate.

*Leaf tip form.*—Acute.

*Leaf color.*—Upper surface—Considered a dull purplish green (RHS Greyed-Purple Group 187 A).

*Leaf color.*—Lower surface—Yellow green (RHS Yellow-Green Group 146 B).

*Leaf texture.*—Glabrous.

*Leaf venation.*—Pinnately veined.

*Mid-vein.*—Color—(RHS Greyed-Red Group 181 B).

*Leaf margins.*—Generally undulate.

*Leaf form.*—Considered crenate.

*Uniformity.*—Considered generally uniform.

*Leaf petioles.*—Size.—Considered medium large.

*Petiole length.*—About 16.0 mm. to about 21.0 mm.

*Petiole diameter.*—About 1.7 mm. to about 2.0 mm.

*Petiole color.*—(RHS Greyed-Orange Group 176 A).

*Leaf glands.*—Size—Generally considered medium small. The leaf glands are about 1 mm. in height and about 1 mm. in width.

*Leaf glands.*—Number—Generally one per side, occasionally 2 or more per side.

*Leaf gland type.*—Reniform, and considered reasonably unappressed relative to the petiole margin.

*Leaf gland color.*—Depending upon the developmental stage, this is generally considered a medium brown (RHS Greyed-Orange Group 175 D).

*Leaf Stipules.*—Size—Generally absent for the variety.

Flower:

*Flower buds.*—Generally—The floral buds, depending upon the stage of development, are approximately 4.0 mm. wide; and about 6.0 mm. long; conic in form; and slightly appressed relative to the bearing shoot.

*Flower buds.*—Color—The bud scales, in an advanced, pre-bloom stage are generally considered a greyish brown (RHS Greyed-Orange Group 165 A). The buds are generally considered hardy under typical central San Joaquin Valley climatic conditions.

*Hardiness.*—No winter injury has been noted during the last several years of evaluation in the central San Joaquin Valley. The current variety has not been intentionally subjected to drought or heat stress, and therefore this information is not available.

*Date of first bloom.*—Observed on March 2 in 2008.

*Blooming time.*—Considered mid-season in relative comparison to other commercial rootstocks grown in the central San Joaquin Valley. Date of full bloom was observed on Mar. 5, 2008. The date of bloom varies slightly depending upon the prevailing climatic conditions, and cultural practices.

*Duration of bloom.*—Approximately 6-9 days. This characteristic varies slightly with the current climatic conditions.

*Flower type.*—The variety is considered to have a showy type flower.

*Flower size.*—Flower diameter at full bloom is approximately 37 mm. to about 41 mm.

*Bloom quantity.*—Considered moderate.

*Flower bud frequency.*—Normally 1 to 2 flower buds appear per node.

*Petal size.*—Generally—Considered small for the species but considered normal for the flower type.

*Petal length.*—Approximately 15.0 mm. to about 19.0 mm.

*Petal width.*—Approximately 8.0 mm. to about 11.0 mm.

*Petal form.*—Obovate.

*Petal count.*—Generally 5.

*Petal texture.*—Pubescent.

*Petal color.*—Light pink approximately (RHS Red Purple Group 62 C).

*Fragrance.*—Slight.

*Petal claw.*—Form—The claw is considered truncate in shape, and has a relatively small size when compared to the overall dimensions of the petal itself.

*Petal length.*—Approximately 5.0 mm. to about 7.0 mm.

*Petal width.*—Approximately 4.0 mm. to about 6.0 mm.

*Petal margins.*—Generally considered gently undulate, from nearly smooth, to moderately undulate.

*Petal apex.*—Generally—The petal apices generally appear entire and without an apical groove.

*Flower pedicel.*—Length—Considered medium small, and having an average length of approximately 3.0 mm. to about 5.0 mm.

*Diameter.*—Considered 2.0 mm. to approximately 3.0 mm.

*Flower pedicel.*—A Greyed brown, (RHS Brown Group N200 B).

*Floral nectaries.*—Color—Depending upon the stage of floral development, it is considered a dull white (RHS White Group 155 A).

*Calyx.*—Color—A dull green (RHS Green Group 138 A).

*Sepals.*—Surface texture—The surface has a short, fine, pubescent texture.

*Size.*—Average, and ovate in form. Approximately 7.0 mm. in length, and about 4.0 mm. in width.

*Sepals.*—Color—A dark purple brown (RHS Brown Group 200 B).

*Anthers.*—Generally—Small in size.

*Anthers.*—Color—Typically yellow-orange (RHS Yellow-Orange Group 22 B).

*Pollen production.*—Pollen is abundant, and has a yellow orange color, approximately (RHS Yellow Orange Group 17 C).

*Filaments.*—Size—Variable, approximately 11.0 mm. to about 13.0 mm. in length.

*Filament color.*—Depending upon the floral maturity, approximately (RHS Red-Purple Group 68 B); nearer to the apex, the color darkens to approximately (RHS Red-Purple Group 70 B).

*Pistil.*—Number—Usually 1.

*Pistil shape.*—Considered long in relation to the general floral dimensions of the variety.

*Pistil length.*—Approximately 22.0 mm. to about 26.0 mm. including the ovary.

*Pistil color.*—Depending upon the floral maturity, it is considered a very pale pink at a location near the ovary (RHS Red-Purple Group 69 A); and the color gradually darkens as you advance in the direction of the style, approximately (RHS Red-Purple Group 63A).

*Pistil surface texture.*—The variety has a pubescent pistil.

*Resistance to insects and disease.*—The present variety shows a lower incidence of crown gall, (*agrobacterium tuberfaciens*) when compared with the 'Hansen 536' rootstock (U.S. Plant Pat. No. 5,173).

Although the new variety of rootstock possesses the described characteristics when grown under the ecological conditions prevailing near Fowler, Calif., in the central part of the San Joaquin Valley of California, it should be understood that variations of the usual magnitude and characteristics incident to changes in growing conditions, fertilization, pruning, pest control and horticultural management are to be expected.

Having thus described and illustrated our new variety rootstock tree, what we claim is new and desire to secure by Plant Letters Patent is:

1. A new distinct variety of rootstock, substantially as illustrated and described, and which is characterized principally as to novelty by its lower incidence and experience of crown gall (*agrobacterium tuberfaciens*) when compared to other common cultivars.

* * * * *

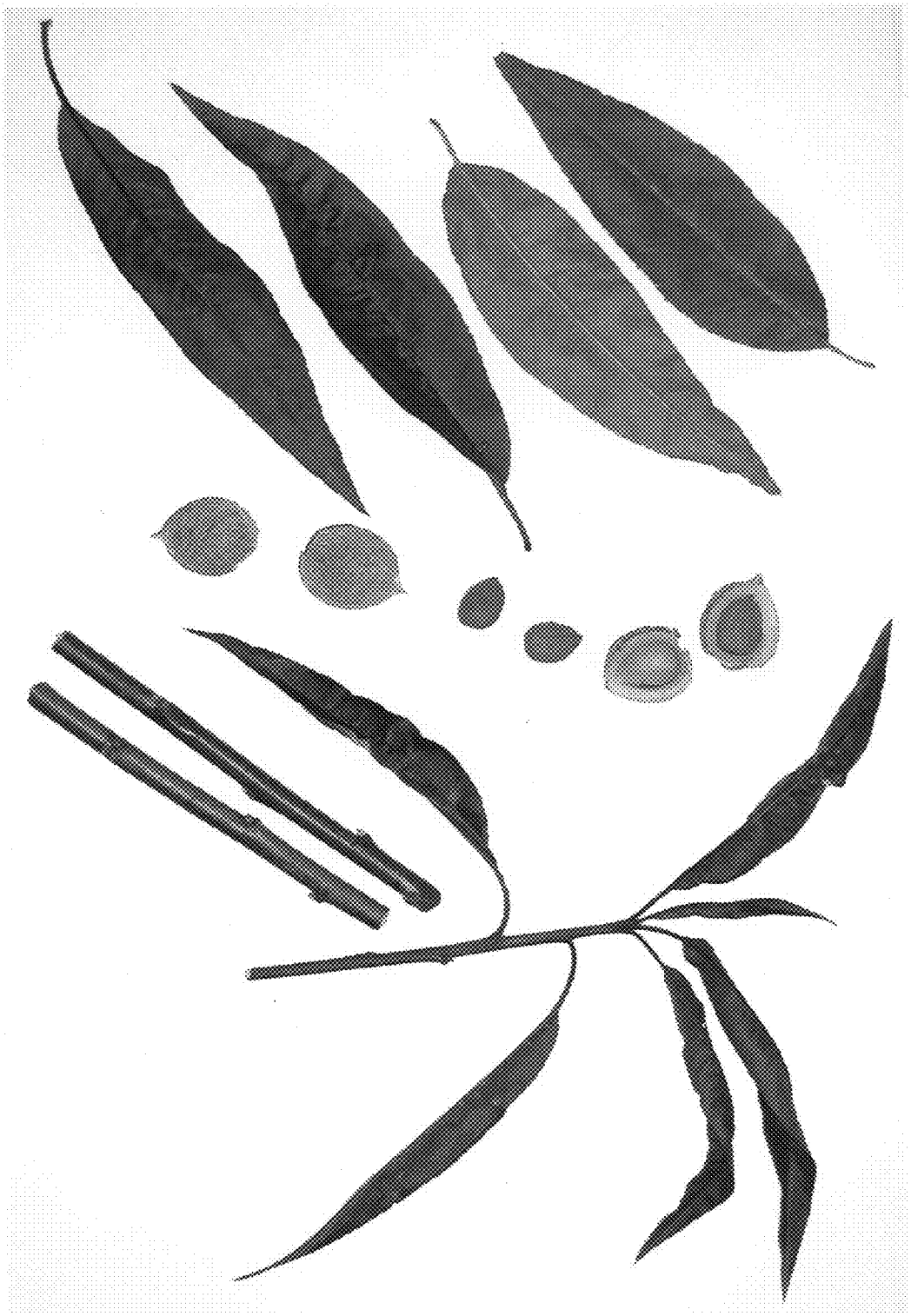

UNITED STATES PATENT AND TRADEMARK OFFICE

CERTIFICATE OF CORRECTION

PATENT NO. : PP21,248 P2
APPLICATION NO. : 12/386894
DATED : August 31, 2010
INVENTOR(S) : John K. Slaughter et al.

It is certified that error appears in the above-identified patent and that said Letters Patent is hereby corrected as shown below:

In the Specification

Column 1, line 19, replace "made in 1987," with --made in 1984,--.

Column 1, line 28, replace "After the 1984 growing season" with --After the 1987 growing season--.

Column 2, line 40, replace "*m. jovinica*" with --*m. javanica*--.

Signed and Sealed this
Eighth Day of July, 2014

Michelle K. Lee

Michelle K. Lee
*Deputy Director of the United States Patent and Trademark Office*